United States Patent [19]

Zeddies et al.

[11] 4,005,710
[45] Feb. 1, 1977

[54] PARENTERAL APPARATUS WITH ONE-WAY VALVE

[75] Inventors: Armand Al Zeddies, Richmond, Va.; Andrew John Muettertis, Waukegan, Ill.

[73] Assignee: Abbott Laboratories, North Chicago, Ill.

[22] Filed: Feb. 12, 1975

[21] Appl. No.: 549,408

[52] U.S. Cl. .............................. 128/214 R; 128/274; 137/533
[51] Int. Cl.² .......................................... A61M 5/14
[58] Field of Search ........ 128/214 R, 214 C, 214.2, 128/227, 274; 137/512.1, 519, 532, 533, 605

[56] References Cited
UNITED STATES PATENTS

| | | | |
|---|---|---|---|
| 1,657,741 | 1/1928 | Carrey | 137/533 |
| 2,007,948 | 7/1935 | Field | 137/533 X |
| 2,866,457 | 12/1958 | Moore | 128/214 R |
| 3,109,444 | 11/1963 | McKee | 137/332 |
| 3,886,937 | 6/1975 | Bobo et al. | 128/214 R |

Primary Examiner—Dalton L. Truluck
Attorney, Agent, or Firm—Robert L. Niblack; Neil E. Hamilton

[57] ABSTRACT

A one-way valve which permits for positive and sensitive action as well as simplified construction in a parenteral solution administration device. Preferably, the valve is formed of a resilient material with a flat surface on one side and has projections extending from the opposite side to engage a wall surface surrounding an outlet orifice. The disc valve is free to move within the valve body and is laterally spaced therefrom to permit fluid to flow around the sidewall and between the projections.

11 Claims, 10 Drawing Figures

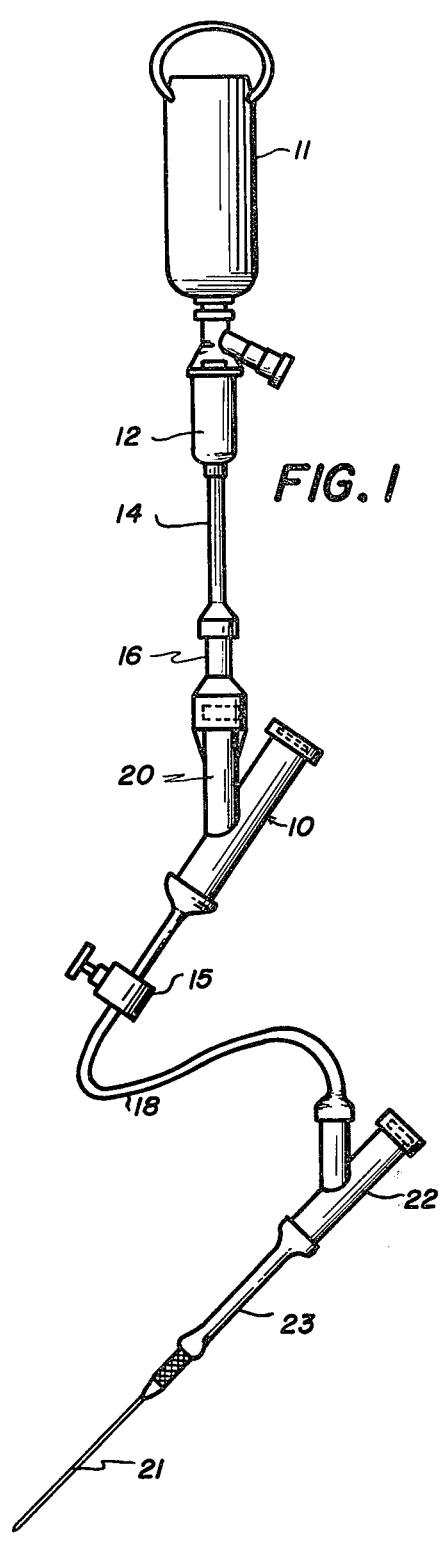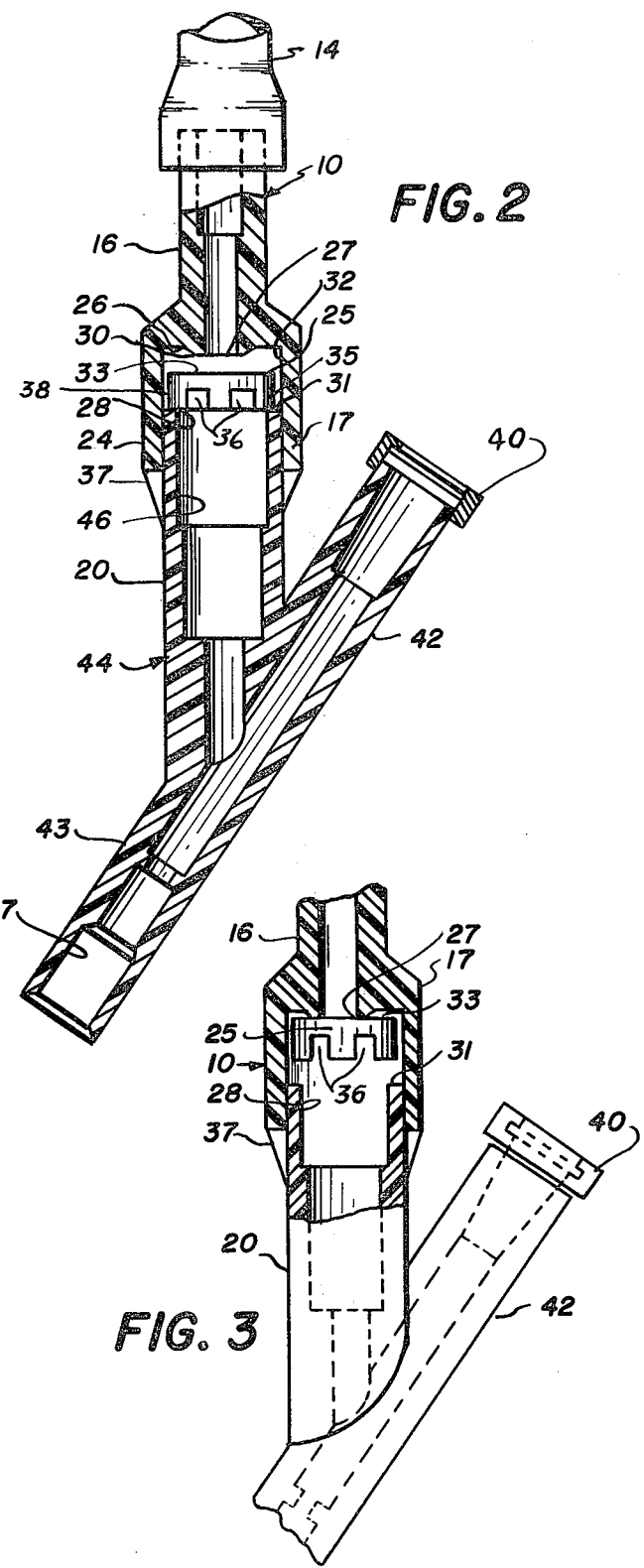

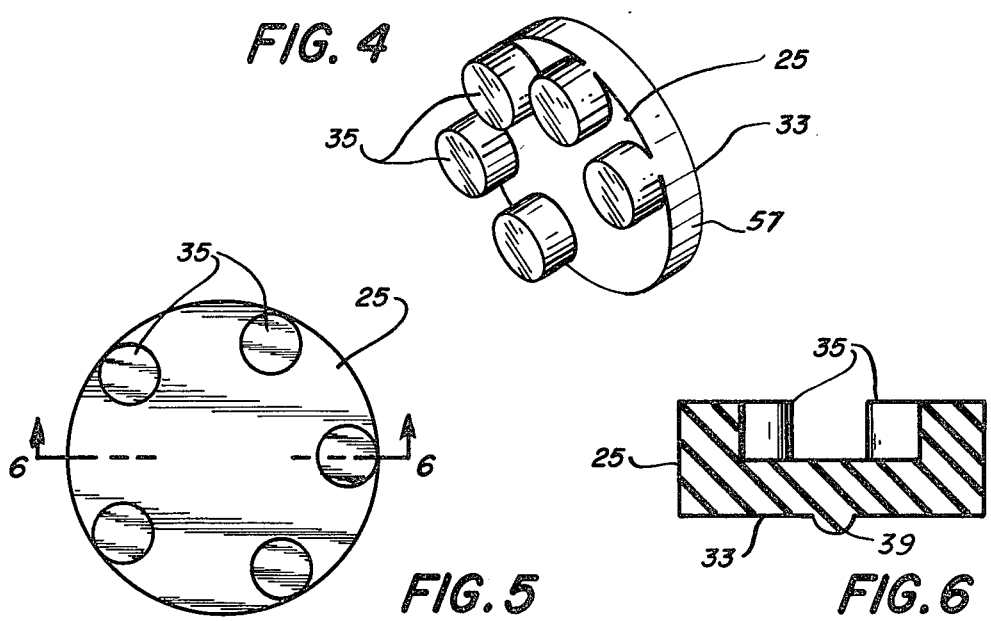
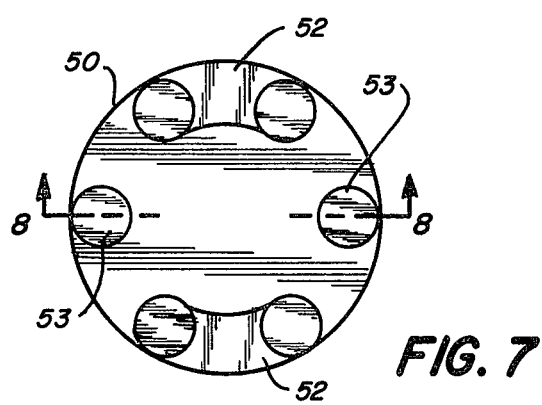
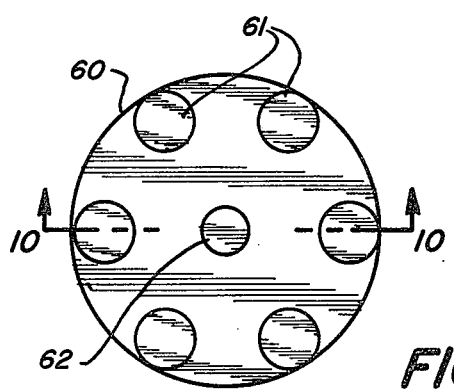
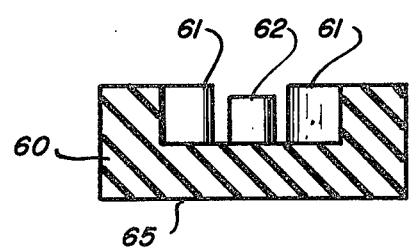

PARENTERAL APPARATUS WITH ONE-WAY VALVE

BACKGROUND OF THE INVENTION

This invention relates to a simplified one-way disc valve. More particularly, this invention relates to a disc-type check valve for use in a parenteral solution administration apparatus wherein the disc valve is constructed so as to be sensitive to fluid flow and does not become jammed or cocked in the valve body.

Valving devices of the type concerned with in this invention are described in U.S. Pat. Nos. 2,538,662; 2,784,733; 2,844,147 and 3,021,841. The problem with many of these prior art check valves is that they require orientation of the movable valve member either over an orifice or into it as shown in U.S. Pat. Nos. 2,538,662; 2,784,733 or 3,021,841. Other prior art devices such as shown in U.S. Pat. No. 2,844,147, have valve body members which are of such a mass that they do not respond quickly and precisely to fluid flow so as to close off an orifice.

It is an advantage of the present invention to provide a novel one-way valve which is sensitive to fluid flow and is constructed so that precise tolerances and interfitting are not required so as to close off an orifice. The present invention provides a valving structure which utilizes pre-existing tubular members to form a valve body. The disc valve of this invention can be mass produced and assembled in a fast and rapid manner so as to be economically attractive.

SUMMARY OF THE INVENTION

The foregoing advantages are accomplished and the shortcomings of the prior art are overcome by the present valving device which is comprised of a valve body defining opposing endwalls and a lateral wall surface with intake and outlet orifices in the endwalls. A freely movable, flexible valve member having a substantially thin body section is positioned between the endwalls and spaced from the lateral wall surface with the valve member presenting a substantially solid surface portion facing the intake orifice. Openings are provided in the valve member in the portion of the valve member facing the outlet orifice so that fluid can flow from the intake orifice, around the lateral side of the valve member, through the openings and ultimately into the outlet orifice. The flow of fluid will cause that portion of the valve member adjacent the wall forming the outlet orifice to rest against this wall. However, with the openings in the valve member facing the outlet orifice, fluid will flow therearound. When fluid is caused to flow in the opposite direction and toward the intake orifice, the freely movable valve member will be carried by it until the side facing the intake orifice comes in contact with the wall defining the intake orifice to thereby seal it from fluid flow. In a preferred embodiment, the valve body is formed from two telescoping tubular members with one of the members having a reduced diameter tubular portion, and the valve member composed only of a small rubber disc with projections extending therefrom and in the direction of the outlet orifice.

BRIEF DESCRIPTION OF THE DRAWINGS

A better understanding of the one-way disc valve of this invention will be accomplished by reference to the drawings wherein:

FIG. 1 is a perspective view of a parenteral solution administration device with the one-way disc valve forming a part thereof.

FIG. 2 is a view in partial vertical section of the valving device showing the disc valve in the open position.

FIG. 3 is a view similar to FIG. 2 except showing the valving device in a closed position.

FIG. 4 is a perspective view of the valve member employed in the valving device of FIGS. 2 and 3.

FIG. 5 is an end view of the valve member shown in FIG. 4.

FIG. 6 is a view in vertical section taken along line 6—6 of FIG. 5.

FIG. 7 is an end view of an alternative embodiment of a valve member which can be utilized in the present invention.

FIG. 8 is a view in vertical section taken along line 8—8 of FIG. 7.

FIG. 9 is a bottom view of still another embodiment of the present invention.

FIG. 10 is a view taken along line 10—10 of FIG. 9.

DESCRIPTION OF THE PREFERRED EMBODIMENT

Proceeding to a detailed description of a preferred embodiment of the present invention, the one-way valve device 10 is shown in FIG. 1 in conjunction with a conventional parenteral solution container 11 having an air-vented drip chamber 12 connected thereto. A length of tubing 14 interconnects the drip chamber 12 with the tubular intake portion 16 of valve device 10. Similarly, a length of tubing 18 is interconnected to the outlet tubular portion 20 and ultimately to a hypodermic needle 21 by means of a Y-type injection site 22 with a length of tubing 23 connecting the needle and the injection site. A flow control clamp 15 is secured to tubing 18.

As best shown in FIGS. 2 and 3, tubular portions 16 and 20 are telescoped and spaced apart to form a valve body 24 with valve member 25 placed in the valve cavity 26. Under normal circumstances, tubular portion 16 will be the intake portion of valve device 10 and will define an intake orifice 27, with tubular portion 20 providing an outlet orifice 28. It will be noted that a raised rim 30 is provided in tubular portion 16 surrounding orifice 27 while the endwall 31 of tubular portion 20 will surround and form orifice 28. A lateral wall surface 32 is provided by tubular portion 16 to complete the valve cavity 26. It will be noted in FIGS. 2 and 3, and will be more particularly described in FIGS. 4 – 10, that valve member 25 is of a disc-type configuration having a substantially flat surface 33 facing the intake orifice 27 and surrounding rim 30. Valve member 25 has a plurality of projections 35 extending from the valve member for engagement with endwall 31 surrounding and forming outlet orifice 28. Projections 35 provide openings or passages 36.

It will be noted in conjunction with FIGS. 2 and 3 that a standard reseal device 40 is provided on the other upper arm portion 42 which is adjacent tubular portion 20 and with tubular portion 43 forms a standard Y-type junction 44. Tubular portion 16 with enlarged diameter section 17 is, in effect, an adapter for fitting over the standard Y-type junction 44. It is aided in its retention thereon in a telescoping manner by means of annular flange 37. It will be seen regarding tubular portions 20 and 43 that there are numerous tapered cavities in the body sections such as shown at 46 and 47. These are not essential and can be eliminated. However, in the instance of cavity 47 in arm portion 43, it can be used to accommodate a length of tubing such as 18.

As indicated earlier, valve member 25 is of a disc-type configuration and has a multiplicity of projections 35 extending therefrom. These features are best shown in FIGS. 4 – 10. Referring specifically to FIGS. 4 – 6, all of the projections 35 are of a uniform dimension and are rounded in configuration. Preferably they have a diameter of 0.040 inch and are spaced 72° apart to provide passages 36 between them. The projections 35 have diameters which are substantially smaller than the spacing between them so as to prevent interwedging of the projections with other discs during handling and cause unwanted sticking. Similarly a small projection 39 extends from flat surface 33 so as to prevent unwanted sticking of the flat surfaces of other discs during processing. This is sometimes a problem because of the type of rubber material employed. However, projection 39 is not of great importance and can be eliminated.

FIGS. 7 and 8 illustrate a further embodiment of a valve member 50 which also has a flat surface 51 with two arcuate-like projections 52 and two circular projections 53. In FIG. 9, a further embodiment of a valve member 60 is shown which is similar to valve members 50 and 25. In this particular embodiment, rounded projections 61 are positioned along the periphery of the valve member. However, in addition, there is a central but smaller rounded projection 62. Valve member 60, as is true of valve members 25 and 50, also has a flat surface 65.

The purpose of having either the circular or rounded projections 35 of a small or larger diameter than the space between them or having the arcuate-type projections 52 and the central post 62 is to prevent the projections from becoming interfitted and sticking together which poses a problem during manufacturing procedures. In all instances, passages such as 36 will be provided between the projections to allow fluid to flow therebetween for purposes as will be explained in the operation. It should be noted that in all of the embodiments in FIGS. 4 – 10 that some of the edges of projections 35, 52, 53 and 61 are coextensive with the edge of the valve bodies. This is to insure that the valve projections seat on endwall 31 in the open position.

Operation

A better understanding of the advantages of the valve device will be had by a description of its operation. As shown in FIG. 1, valving device 10 will be interconnected to solution container 11 by means of drip chamber 12 and tubing 14. Parenteral solution will be allowed to flow from the container into hypodermic needle 21 when clamp 15 is open. The position of valve member 25 will be as shown in FIG. 2 with projections 35 resting against endwall 31 of tubular member 20. In this position fluid will flow around the lateral surface 38 of valve member 25 as it is spaced from sidewall 32 of tubular portion 16. Fluid will continue to flow between projections 35 and passages 36, through outlet orifice 28 into tubular portion 20 and ultimately to hypodermic needle 21. Should it be desired to administer a second solution, and not simultaneously with the solution in container 11, this is afforded by means of reseal device 40 where a second solution can be injected therethrough. When this takes place, fluid will flow in through tubular portion 42 and attempt to back up into tubular portion 20. This will effect an upward movement of valve member 25 which will cause the flat surface 33 to seat against rim 30 and thereby seal off intake orifice 27. The valve member will remain in this position as long as fluid is introduced into tubular portion 42 at a pressure greater than that of fluid passing in through tubular portion 16. When fluid is discontinued being introduced into tubular portion 42 and upwardly into portion 20, valve member 25 will move to the open position due to greater pressure of fluid in tubular portion 16; onto the endwall 31 of tubular portion 20 to thereby retain its position as shown in FIG. 2 in the open position with fluid flowing into intake orifice 27 and out through outlet orifice 28 and around valve member 25.

It will be seen in the foregoing description that valve member 25 is free to move in valve cavity 26. However, no exact positioning of the valve member is necessary as any portion of the flat surface 33 coming in contact with rim 30 will seal off intake orifice 27. Projections 35 afford a dual function of permitting passage of fluid around the end of the valve member without sealing it against an associated wall surface. It will be noted that valve member 25 has a relatively thin body section 57 which is equal to in width of the length of projections 35. This permits the valve member 25 to be designed so that it is not massive and is responsive to fluid flow. Preferably the height of valve member 25 is 0.040 inch with projections extending therefrom 0.040 inch. The preferred diameter of valve member 25 is 0.205 inch and it has a specific gravity of 0.93 – 0.91.

Valve body members 50 and 60 operate in the same manner as previously described for valve member 25 and have the same important size relationship between body sections and projections.

It will thus be seen that through the present invention there is now provided a one-way valve which is positive in its operation and simple in its construction. The valve cavity can be easily formed from two telescoping tubular members and the disc-type valve members 25, 50 and 60 are formed with flat surfaces which do not require any type of orientation with an orifice for operation. Consequently, they are not subject to becoming misaligned or jammed. Further, a minimum amount of material is utilized in forming the valve members so that they are very sensitive to minimal fluid flow.

The foregoing invention can now be practiced by those skilled in the art. Such skilled persons will know that the invention is not necessarily restricted to the particular embodiments present herein. The scope of the invention is to be defined by the terms of the following claims as given meaning by the preceding description.

We claim:

1. A one-way valve for use in an apparatus for administering a parenteral solution to a patient comprising a valve body defining opposing end walls and a lateral wall surface with an intake orifice and an outlet orifice in said end walls, a freely movable, flexible valve member having a substantially thin body section with a width of a given dimension positioned between said end walls and spaced from said lateral wall surface, said valve member presenting a substantially solid surface portion facing said intake orifice, a plurality of substantially, uniformly spaced projections extending from said body section in one direction from one side of said valve member and inwardly over said body section within the extended confines of said body section to define a plurality of uniformly spaced openings between said projections in the valve member facing the outlet orifice, said projections having approximately the same height as said given width dimension for said body section and another projection extending from said body section from the other side thereof in a direction opposite to said plurality of projections and positioned substantially centrally with respect to said body section, said valve member constructed and arranged to be freely positioned in said valve body without substantial contact with said lateral wall surface of said valve body.

2. The apparatus as defined in claim 1 wherein said solid surface portion of said flexible valve member is substantially flat.

3. The apparatus as defined in claim 1 wherein said valve body is defined by two opposing telescoping tubular members with the outlet orifice defined by one of the tubular members which is of a smaller diameter.

4. The apparatus as defined in claim 1 wherein said projections are of a uniform dimension.

5. The apparatus as defined in claim 4 wherein said projections are of a rounded configuration and are spaced equidistantly along the periphery of said valve member.

6. The apparatus as defined in claim 5 wherein the rounded members have a diameter smaller than the spacing between them.

7. The apparatus as defined in claim 5 wherein one of said plurality of projections is centrally positioned in said valve member.

8. The apparatus as defined in claim 7 wherein some of said projections are elongated with an arcuate configuration with some of the edges of said projections being coextensive with the edge of said valve body.

9. The apparatus as defined in claim 1 wherein said valve member is composed of a rubber composition.

10. The apparatus as defined in claim 3 wherein said tubular member defining said outlet orifice forms a Y-type tubular junction to which is attached a needle assembly at one end, and a solution container, drip chamber and entry site for a fluid at the opposite end.

11. The apparatus as defined in claim 10 wherein said entry site is composed of a reseal device.

* * * * *